United States Patent [19]

Pfeiffer

[11] 4,395,401

[45] Jul. 26, 1983

[54] RENALLY ACTIVE DIPEPTIDES

[75] Inventor: Francis R. Pfeiffer, Cinnaminson, N.J.

[73] Assignee: SmithKline Beckman Corporation, Philadelphia, Pa.

[21] Appl. No.: 300,546

[22] Filed: Sep. 9, 1981

[51] Int. Cl.³ .................... A61K 37/00; C07C 103/52
[52] U.S. Cl. .............................. 424/177; 260/112.5 R
[58] Field of Search ................. 260/112.5 R; 424/177

[56] References Cited

U.S. PATENT DOCUMENTS 4,016,042  4/1977  Svendsen .................... 260/112.5 R

FOREIGN PATENT DOCUMENTS 830911  11/1975  Belgium .
2943582  5/1980  Fed. Rep. of Germany .
WO80/00252  2/1980  PCT Int'l Appl. .

*Primary Examiner*—Delbert R. Phillips
*Attorney, Agent, or Firm*—William H. Edgerton; Richard D. Foggio; Alan D. Lourie

[57] ABSTRACT

A group of prolyl-α-lower alkylphenylalanine dipeptides have been found to improve kidney function especially on cumulative administration. A species is N-4-(4'-hydroxyphenyl)-butyryl-L-propyl-D,L-α-methyl-3,4-dimethoxyphenylalanyl-L-arginine.

11 Claims, No Drawings

RENALLY ACTIVE DIPEPTIDES

This invention comprises a new group of chemical compounds whose structures have a prolyl-α-lower alkylphenylalanine nuclear skeleton with specific substitution patterns found necessary for the described biological activity. The utility of the compounds is to improve kidney function and thereby to lower abnormal blood pressure.

DESCRIPTION OF THE ART

Belgian Pat. No. 830,911 describes a series of prolylphenylalanyl-arginine tripeptides having a ω-phenylpropionyl at the proline ring nitrogen and an aromatic substituent at the other terminal amino group which are useful in certain analytical procedures. Certain tripeptides alleged to have bradykinin inhibitory activity including prolylphenylalanylarginine chains are described in PCT specification I.P. No. W080/00252. DT 2,943,582 discloses a number of prolylphenylalanylarginine tripeptides as the naphthyl esters useful as substrates for various enzymes. The present invention is comprised of compounds whose structures differ in several critical parameters over and whose utilities are quite different from those in the art.

DESCRIPTION OF THE INVENTION

The new chemical compounds of this invention have structures which are distinquished by having a prolyl-α-lower alkylphenylalanine dipeptide chain substituted at the ring N-member of the proline ring with a ω-phenylbutyryl group and at the amino group of the alanylamide structure with α-carboxy-ω-guanidinobutyl, ω-guanidinopropyl or ω-aminopropyl. Structural features critical to preserve biological activity of these compounds are the α-alkyl group and the butyryl chain of the compounds. Exemplary of the compounds of this invention are those represented by the Formula I:

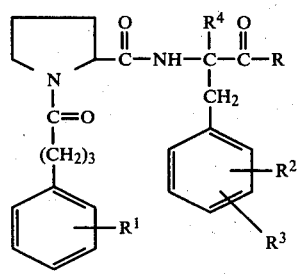

in which;
R is N-arginyl

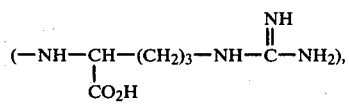

ω-quanidinopropylamino

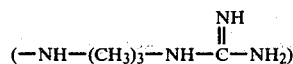

or ω-aminopropylamino (—NH—(CH$_2$)$_3$—NH$_2$);

$R^1$, $R^2$ or $R^3$ each represent hydrogen, methoxy or hydroxy; and
$R^4$ is lower alkyl of 1–3 carbons especially methyl.

A subgeneric group of new compounds of this invention are those of Formula I in which R is N-arginyl. A second group are those in which R in N-arginyl and $R^1$–$R^3$ are each hydroxy or methoxy. As stated above $R^4$ is preferably methyl.

Also included in this invention are the pharmaceutically acceptable, acid addition salts of the compounds of Formula I such as those prepared by reacting the bases with hydrochloric acid, sulfuric acid, sulfamic acid, phosphoric acid, acetic acid, maleic acid, methane sulfonic acid or hydrobromic acid. Such salts are prepared by methods known to the art.

The compounds of this invention are prepared by reaction sequences which involve as a key step formation of the amide group present between the prolyl fragment and the α-alkylphenylalanyl fragment or the latter and the arginyl-like fragment.

Reaction Sequence A

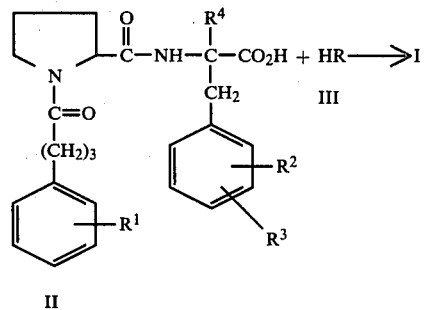

Reaction Sequence B

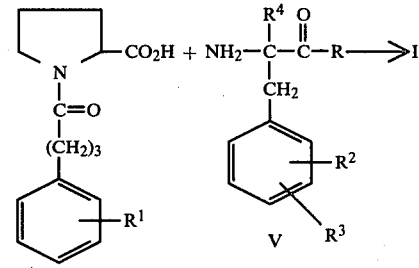

In the formation of the amide bond in Reaction Sequences A and B, standard peptide coupling methods are used. Especially useful is the reaction of the carboxylic acid (II or IV) with the amine (III or V) in the presence of a dehydrating coupling agent such as dicyclohexylcarbodiimide in a suitable organic solvent such as tetrahydrofuran, dimethylacetamide or dimethylformamide at moderate temperatures, such as room temperature, until reaction is complete, from 1–12 or more hours.

In the Reaction Sequences A and B, R→$R^4$ are as defined above or are precursor groups such as an ester, ether, nitro or benzyl derivative which generate the desired end or intermediate products after regenerative hydrolytic or hydrogenation reactions. The new compounds of Formula II are valuable intermediates and a part of this invention. Reaction Sequence A is the more useful route of preparation.

The compounds of this invention have pharmacodynamic activity and as such are useful pharmaceutical compounds. More specifically they increase renal blood flow and decrease renal vascular resistance as does dopamine. Their effect in improving kidney function appears to be cumulative. These compounds therefore, are long acting antihypertensive agents.

The biological activity of the compounds of Formula I was demonstrated by administering the compounds by infusion to anesthetized dogs measuring the mean arterial blood pressure, renal blood flow, renal vascular resistance and heart rate in the test procedure explained in detail in U.S. Pat. No. 4,197,297. Generally speaking the compounds gave a decreased renal vascular resistance and/or increased renal blood flow at doses ranging from 1/10 to 1/100 that for dopamine. Specific results are included in the examples.

One skilled in the art will recognize that the compounds of this invention may exist in various configurations such as optical isomers or mixtures thereof. Such compounds are easily prepared by substituting the desired amino acids into the chemical reactions of the examples which illustrate this invention. Also the proline ring in the compounds of Formula I may be replaced by other prolyl-like fragments such as dehydroprolyl

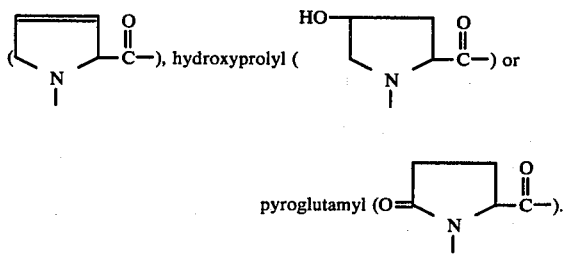

The following examples are intended to teach the preparation and use of the new compounds of this invention but not to limit its scope. All temperatures are expressed in degrees Centigrade.

EXAMPLE 1

A mixture of 15.13 g. (0.0626 m.) of L-proline benzyl ester hydrochloride, 11.3 g. (0.628 m.) of 4-(4'-hydroxyphenyl)-butyric acid, 17.0 g. (0.126 m.) of 1-hydroxybenzotriazole, 12.0 ml. of N-ethylmorpholine, 40 ml. of dimethylformamide, 80 ml. of tetrahydrofuran and 13.0 g. (0.063 m.) of dicyclohexylcarbodiimide was stirred for 3 hours at room temperature. The mixture was filtered and the tetrahydrofuran removed in vacuo from the filtrate which was then diluted with water and ethyl acetate. The resulting mixture was acidified with dilute hydrochloride acid. The layers were separated. The organic layer was extracted several times with ethyl acetate. The organic extracts were washed with dilute acid, water, bicarbonate solution and brine then dried and evaporated to give a syrup which was taken through a silica gel column with methylene chloride then 1% methanol in methylene chloride to give 18.9 g. (83%) of N-4-(4'-hydroxyphenyl)-butyrylproline benzyl ester, m/e=367.

This material (18.9 g., 0.051 m.) was dissolved in 100 ml. of ethyl alcohol and hydrogenated over 2.5 g. of 10% palladium-on-charcoal. The mixture was filtered and the filtrate evaporated to give 15 g. of the desired free acid, m/e 277.

The N-acylproline (2.8 g., 0.01 m.) was mixed with 2.9 g. (0.01 m.) of D,L-α-methyl-3,4-dimethoxyphenylalanine methyl ester hydrochloride, 2.7 g. (0.02 m.) of 1-hydroxybenzotriazole, 2.0 ml. of N-ethylmorpholine, 2.06 g. (0.01 m.) of dicyclohexylcarbodiimide, 20 ml. of dimethylformamide and 40 ml. of tetrahydrofuran. The mixture was stirred at room temperature for 72 hours.

The reaction mixture was filtered. The filtrate was concentrated. The residue was taken up in ethyl acetate and washed with dilute acid, water bicarbonate and brine. The organic extract was dried and evaporated to give 5.12 g. of N-4-(4'-hydroxyphenyl)-butyryl-L-prolyl-D,L-α-methyl-3,4-dimethoxyphenylalanine methyl ester, m/e 512, an important intermediate of the invention.

The ester dipeptide (5.0 g., 9.77 mm.), 45 ml. of methyl alcohol and 2.5 ml. of 2.5 N sodium hydroxide solution were mixed and stirred for 17 hours. The methanol was taken off and the residue taken up in water and filtered. The aqueous solution was acidified with conc. hydrochloric acid to give a solid which was taken into methylene chloride. After washing with water, the methylene chloride extract was dried and evaporated to give 3.2 g. of the desired new dipeptide intermediate as the free acid, m/e 498.

Dicyclohexylcarbodiimide (1.28 g., 6.2 mm) was added to a mixture of 3.1 g. (6.2 mm.) of the dipeptide acid (Formula II, $R^1$=4-hydroxy, $R^2$=3-methoxy, $R^3$=4-methoxy), 1.67 g. (6.2 mm) of ω-nitro-L-arginine, methyl ester, hydrochloride, 1.68 g. (12.4 mm.) of 1-hydroxybenzotriazole, 3.0 ml. of N-ethylmorpholine, 10 ml. of dimethylformamide and 30 ml. of dry tetrahydrofuran. The resulting mixture was stirred at room temperature for 54 hours. The mixture was filtered and the filtrate diluted with iced brine, dilute hydrochloric acid and ethyl acetate. The organic extract was washed as above, dried and evaporated to give 3.8 g. of N-4-(4'-hydroxyphenyl)-butyryl-L-prolyl-D,L-α-methyl-3,4-dimethoxyphenylalanyl-ω-nitro-L-arginine methyl ester; m/e, M+1=666.6.

This material (3.5 g.) was stirred in 60 ml. of methyl alcohol and 20 ml. of 2.5 N sodium hydroxide solution at 25° for 17 hours. The alcohol was evaporated off. The residue was suspended in water and filtered. The filtrate was acidified with concentrated hydrochloric acid to give a buff colored solid which was dissolved in ethyl acetatemethanol. The extract was washed with brine, dried and evaporated to give 1.99 g. of the desired acid, m/e, M+1=700.

A mixture of 1.75 g. of this ω-nitro-tripeptide acid, 2.5 g. of 10% palladium-on-barium sulfate, 50 ml. of ethyl alcohol and 30 ml. of glacial acetic acid was hydrogenated at low pressure. The product had some starting material present as demonstrated by thin layer chromatography. The material was hydrogenated again with fresh catalyst for 8 hours. The catalyst was removed and the hydrogenation solution was evaporated. The residue was recrystallized first with toluene then ethyl alcohol to give 1.3 g. of buff colored solid, m.p. 122°-125° as the hydrated 1.5 acetic acid salt; $[\alpha]_D^{25}$ = −44° (cl, $H_2O$), m/e 688, N-4-(4'-hydroxyphenyl)-butyryl-L-prolyl-D,L-α-methyl-3,4-dimethoxyphenylalanyl-L-arginine acetic acid salt.

Anal. Calcd. for $C_{33}H_{46}N_6O_8 \cdot 1.5HOAc \cdot 3H_2O$: C, 54.13; H, 7.07, N, 10.52. Found: C, 53.99, 53.69, H, 6.76, 6.71; N, 9.92, 9.87.

This compound administered by infusion to three anesthetized dogs at 30 μg/kg/min significantly decreased renal vascular resistance (−21.3 ) and increased renal blood flow (+18%). In secondary testing it had an $ED_{15}$ of 506 μg/kg. Dopamine is 3.5 μg/kg.

EXAMPLE 2

A mixture of 2.25 g. (4.5 mm.) of N-4-(4'-hydroxyphenyl)-butyryl-L-prolyl-D,L-α-methyl-3,4-dimethoxyphenylalanine, 1.22 g. (9.0 mm.) of 1-hydroxybenzotriazole, 1.0 g. (4.5 mm.) of N-carbobenzyloxy-1,3-diaminopropane, 4 ml. of N-ethylmorpholine, 0.93 g. (4.5 mm.) of dicyclohexylcarbodiimide, 30 ml. of dry tetrahydrofuran and 10 ml. of dimethylformamide is stirred at ambient temperature for 72 hours. The product is isolated as in Example 1 to give 2.9 g. of the carbobenzoxy dipeptide which is taken over a silica gel column, m/e 688.

This material, 1.6 g., is hydrogenated at low pressure with 2.0 g. of 10% palladium-on-charcoal in 60 ml. of ethanol and 20 ml. of glacial acetic acid. The filtered mixture is then concentrated. The residue is taken up in ethanol and acidified with ethereal hydrogen chloride to give 1.1 g. of N-4-(4'-hydroxyphenyl)-butyryl-L-prolyl-D,L-α-methyl-3,4-dimethoxyphenylalanine 3-aminopropylamide hydrochloride, m.p. 136°–140°, $[\alpha]_D^{25} = -50.8°$ (c1, $H_2O$).

Anal. Calcd. for $C_{30}H_{43}N_3O_5 \cdot HCl \cdot \frac{3}{4}H_2O$: C, 59.59; H, 7.42,; N, 9.27. Found: C, 59.24; H, 7.83; N, 9.06.

This compound administered by infusion at 3 μg/kg/min decreased renal vascular resistance (−11%) and increased renal blood (+13.5%) as well as at 30 and 300 μg/kg/min.

EXAMPLE 3

N-4-(4'-Hydroxyphenyl)-butyryl-L-proline (2.77 g., 0.01 m.) was reacted with 2.46 g. (0.01 m.) of D,L-α-methyltyrosine, methyl ester, hydrochloride by the dicyclohexylcarbodiimide route of Example 1 to give 4.8 g. of N-4-(4'-hydroxyphenyl)-butyryl-L-prolyl-D,L-α-methyltyrosine, methyl ester, m/e=468. This material (4.8 g.) was hydrolized in alcoholic alkali to give the new intermediate acid (Formula II, $R^1$=4-OH, $R^2$=H, $R^3$=4-OH), m/e 454. This material (3.94 g., 8.7 mm.) was reacted with 2.34 g. (8.7 mm.) of ω-nitro-L-arginine, methyl ester, hydrochloride as above to give, after hydrolysis and reduction, 1.98 g. of buff colored solid N-4-(4'-hydroxyphenyl)-butyryl-L-prolyl-D,L-α-methyltyrosyl-L-arginine acetic acid salt; m.p. 148°–150°.

Anal. Calcd. for $C_{31}H_{42}N_6O_7 \cdot CH_3CO_2H \cdot C_2H_5OH$: C, 59.47; H, 7.40; N, 11.89. Found: C, 59.03, 58.93; H, 7.29, 7.29; N, 10.27, 10.21.

This compound at 3, 30 and 300 μg/kg/min decreased renal vascular resistance (−12, −9, −11) and increased renal blood flow (+8.0, +12.0, +11.0) in the anesthetized dog. It also increased renal blood flow 28% after a cumulative dose at 3, 30 and 300 μg/kg/min.

EXAMPLE 4

Using the method of Example 2, 1.04 g. (2.3 mm.) of N-4-(4'-hydroxyphenyl)-butyryl-L-prolyl-D,L-α-methyltyrosine methyl ester was reacted with 6.56 g. (2.3 mm.) of N-carbobenzyloxy-1,3-diaminopropane to give 0.37 g. of N-4-(4'-hydroxyphenylbutyryl)-L-prolyl-D,L-α-methyltyrosine ω-aminopropylamide, hydrochloride, m.p. 154°–156°, m/e 510, $[\alpha]_D^{25} = -44.9°$ (c1, $H_2O$).

This compound at 3 μg/kg/min decreased renal vascular resistance (−9.5) and increased renal blood flow (+8.5 ) in the anesthetized dog.

EXAMPLE 5

Using the method of Example 1, 6.93 g. (0.025 m.) of N-4-(4'-hydroxyphenyl)-butyryl-L-proline was condensed with 5.74 g. (0.025 m.) of D,L-α-methylphenylalanine methyl ester hydrochloride to give, after hydrolysis, 8.35 g. of N-(4-(4'-hydroxyphenyl)-butyryl-L-prolyl-D,L-α-methylphenylalanine, m/e 438 (Formula II, R=OH, $R^2$ and $R^3$=H).

This dipeptide acid (4.38 g., 0.01 m.) was reacted with 2.45 g. (0.01 m.) of N-carbobenzyloxy-1,3-diaminopropane as above to give, after hydrogenation, 2.4 g. of N-4-(4'-hydroxyphenylbutyryl)-L-prolyl-D,L-α-methylphenylalanine ω-aminopropylamide, hydrochloride, m.p. 128°–130°, m/e 496 for free base, $[\alpha]_D^{25} = -51.5°$ (c1, $H_2O$).

Anal. Calcd. for $C_{28}H_{38}N_4 \cdot HCl \cdot \frac{1}{2}H_2O$: C, 62.27; H, 7.46; N, 10.37. Found: C, 62.26; H, 7.40; N, 10.06.

This compound at 300 μg/kg/min infused in three anethetized dogs decreased vascular renal resistance (11.3%) and increased renal blood flow (+11.7%). It also demonstrated a cumulative drug effect.

EXAMPLE 6

The dipeptide acid from Example 5 (2.19 g.) was converted by the method of Example 1 to give 2.0 g. of N-4-(4'-hydroxyphenyl)-butyryl-L-prolyl-D,L-α-methylphenylalanyl-L-arginine 1.5HOAc.1H2O, m.p.=104°–106°, $[\alpha]_D^{25} = -44.7°$ (c1, $CH_3OH$).

This compound in one dog increased renal blood flow at 30 (+12%) and 300 (+11%) μg/kg/min.

EXAMPLE 7

N-(Phenylbutyryl)-L-proline (1.17 g., 4.45 mm.) was reacted as above with 1.30 g. (4.45 mm.) of D,L-α-methyl-3,4-dimethoxyphenylalanine methyl ester hydrochloride to give, after hydrolysis, 2 g. of a syrup, N-(phenylbutyryl)-L-prolyl-D,L-α-methyl-3,4-dimethoxyphenylalanine (Formula II, $R^1$=H, $R^2$=3-OCH3 and $R^3$=4-OCH3). This material was then reacted further as described above to give 0.95 g. of N-(phenylbutyryl)-L-prolyl-D,L-α-methyl-3,4-dimethoxyphenylalanyl-L-arginine acetic acid salt; m.p. 145°–148°, m/e 639, $[\alpha]_D^{25} = -48.5°$ (c1, $CH_3OH$).

Anal. Calcd. for $C_{33}H_{46}N_6O_7 \cdot HOAc \cdot 2H_2O$: C, 57.20; H, 7.39; N, 11.45. Found: C, 56.75, 57.07; H, 6.98, 6.91; N, 11.46, 11.63.

EXAMPLE 8

A mixture of 10 mmoles of N-4-(4'-hydroxyphenyl)-butyryl-L-prolyl-D,L-α-methyl-3,4-dimethoxyphenylalanine, 10 mmoles of 3-aminopropylguanidine dihydrobromide (Chem. Abst. 23, 1880), 20 mmoles of 1-hydroxybenzotriazole, 8 ml. of N-ethylmorpholine, 10 mmoles of dicyclohexylcarbodiimide, 30 ml. of dry tetrahydrofuran and 20 ml. of dimethylformamide is stirred at 25° for 18 hours. After filtration, the filtrate is evaporated. The residue is dissolved in ethyl acetate. The extract is washed with 3% aqueous acetic acid, water and 5% sodium bicarbonate solution. The dried concentrated residue is dissolved in methyl alcohol and added dropwise to 5:1 ether-petroleum ether to give N-4-(4'-hydroxybutyryl-L-prolyl-D,L-α-methyl-3,4-dimethoxyphenylalanine 3-quanidinopropylamide as an amorphous solid.

EXAMPLE 9

A mixture of 6.4 g. (0.0358 m.) of D,L-α-methylphenylalanine, 9.38 g. (0.043 m.) of di-tert.-butyldicarbonate, 5.0 ml. of triethylamine and 100 ml. of dimethylformamide was stirred 20 hours at room temperature. The mixture was filtered, The filtrate was evaporated to give a residue which was taken up in ethyl acetate. The extract was washed with water, cold 1 N hydrochloric acid and water. The dried organic extract was evaporated to give a syrup which solidified and was crystallized from hexane-ether, 4.6 g. (46%) of N-tert.-butoxycarbonyl-D,L-α-methylphenylalanine, m.p. 134°-135°.

This material (4.4 g., 0.016 m.) was suspended in dry tetrahydrofuran and reacted with 4.94 g. of dicyclohexylcarbodiimide, 4.3 g. of ω-nitro-L-arginine, methyl ester hydrochloride, 4.32 g. of 1-hydroxybenzothiazole and 2.76 g. of N-ethylmorpholine at 0° for 1 hour then at room temperature for 72 hours. Working up as above gave 6.8 g. (86%) of N-tert.-butoxycarbonyl-D,L-α-methylphenylalanyl-α-nitro-L-arginine methyl ester, m.p. 143°-145°. $[\alpha]_D^{25}$ (cl, CH$_3$OH)=−33.9°.

Anal. Calcd. for $C_{22}H_{34}N_6O_7$: C, 53.43; H, 6.93; N, 16.99. Found: C, 53.09; H, 6.82; N, 16.61.

This t-boc 23.0 g. (46.6 mm.) and 9.2 ml. (70 mm.) of m-methoxyanisole were suspended in methylene chloride at 0°. After 15 minutes stirring, the mixture was evaporated and ethereal hydrogen chloride added. The separated solid was dissolved in water and washed with ether. The aqueous layer was evaporated under vacuo to give 13.5 g. (67%) of D,L-α-methylphenylalanyl-ω-nitro-L-arginine, methyl ester, hydrochloride, $[\alpha]_D^{25}$ (cl, H$_2$O)=−32.8°.

Anal. Calcd. for $C_{17}H_{26}N_6O_5 \cdot HCl \cdot \frac{1}{2}H_2O \cdot \frac{1}{2}C_2H_5OH$: C, 46.70; H, 6.75; N, 18.15. Found: C, 46.31; H, 6.72; N, 18.11.

This dipeptide was condensed with N-4-(4'-hydroxyphenyl)-butyrylproline as described in Example 1 to give, after deblocking of the protecting groups, the compound cited in Example 1.

This same dipeptide (1.5 g.) is reacted with N-4(4'-methoxyphenyl)-butyryl-D,L-proline using the dicyclohexylcarbodiimide procedure above with hydrolysis of the ester and reduction to give N-4-(4'-methoxyphenyl)-butyryl-L-prolyl-D,L-α-methylphenylalanyl-L-arginine isolated as the base. The acid addition salts are prepared by reacting the base with ether-alcohol containing the desired acid such as hydrogen chloride or methanesulfonic acid.

EXAMPLE 10

A mixture of 3.5 g. (0.005 cm.) of N-(ω-phenyl)-butyryl-L-prolyl-D,L-α-methylphenylalanine ω-N-carbobenzoxyaminopropylamide, prepared by the method of Example 5 using N-phenylbutyryl-L-proline, 300 mg. of palladium-on-carbon and 50 ml. of alcohol was hydrogenated at moderate pressure for 4 hours. The product was worked up as above to give 2.7 g. of N-(ω-phenyl)-butyryl-L-prolyl-D,L-α-methylphenylalanine ω-aminopropylamide as the base.

An aliquot of the base (0.4 g.) is dissolved in methanol and treated with ethanolic hydrogen chloride. Ether was added to separate a solid which after washing and drying was 0.17 g. of the monohydrochloride hydrate.

The salt melted at 98°-102°, $[\alpha]_D^{25}$ (c0.5 CH$_3$OH)=−52.2°.

Anal. Calc'd. for $C_{28}H_{38}N_4O_3 \cdot HCl \cdot H_2O$: C, 63.09; H, 7.75; N, 10.51. Found: C, 62.94; H, 7.74; N, 10.67.

EXAMPLE 11

A mixture of 4.6 g. (7.4 mm.) of N-(ω-phenyl)-butyryl-L-prolyl-D,L-α-methylphenylalaninyl-ω-nitro-L-arginine, prepared as in Example 1 with appropriate unsubstituted starting materials, and 50 ml. of a 50:50 solution of ethyl alcohol and acetic acid was added to a slurry of 2 g. of palladium-on-barium sulfate in ethyl alcohol then hydrogenated for 10 hours. The mother mixture was worked up as described above to give 1.6 g. (37%) of N-(ω-phenyl)-butyryl-L-prolyl-D,L-α-methylphenylalanyl-L-arginine, m.p. 120°-125°, $[\alpha]_D^{25}$ (cl, 1.5, CH$_3$OH)=−53.0°.

Anal. Calc'd. for $C_{31}H_{42}N_6O_5 \cdot 2CH_2O$: C, 59.52, H, 7.60; N, 13.43. Found: C, 59.39, 59.47; H, 7.26, 7.62; N, 13.27, 13.50.

The new chemical compounds described above are incorporated into dosage unit forms and used in methods for improving renal function, treating high blood pressure or treating shock using standard methods as disclosed in the above referenced U.S. Pat. No. 4,197,297 at line 19 column 6 to line 48 column 7 as well as Examples 8 and 9. The doses of the present compounds in the pharmaceutical dosage unit will be an effective nontoxic quantity selected from 50–500 mg. of active base, preferably 75–250 mg. These are administered to patients in need of treatment for the noted clinical conditions from 1–5 times daily.

What is claimed is:

1. A chemical compound of the structural formula:

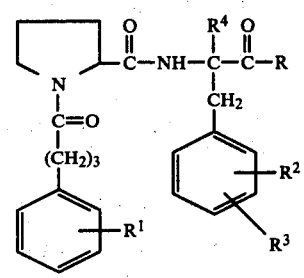

in which:
R is

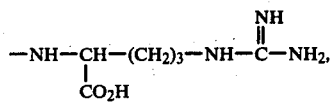

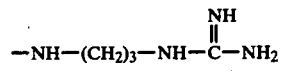

or —NH—(CH$_2$)$_3$—NH$_2$;

R$^1$, R$^2$ or R$^3$ are each hydrogen, hydroxy or methoxy; and

R$^4$ is lower alkyl of 1-3 carbons; or pharmaceutically acceptable acid addition salts thereof.

2. A compound of claim 1 in which R$^4$ is methyl.

3. A compound of claim 1 in which at least one of R$^1$, R$^2$ or R$^3$ is hydroxy or methoxy.

4. A compound of claim 1 in which R is —NH(CH$_2$)$_3$—NH$_2$.

5. The compound of claim 1 being N-4-(4'-hydroxyphenylbutyryl)-L-prolyl-D,L-α-methyl-3,4-dimethoxyphenylalanyl-L-arginine or a pharmaceutically acceptable acid addition salt thereof.

6. The compound of claim 1 being N-4-(4'-hydroxyphenylbutyryl-L-prolyl-D,L-α-methylphenylalanine-3-aminopropylamide or a pharmaceutically acceptable acid addition salt thereof.

7. The compound of claim 1 being N-4-(4'-hydroxyphenylbutyryl)-L-prolyl-D,L-α-methyltyrosyl-L-arginine or a pharmaceutically acceptable acid addition salt thereof.

8. The compound of claim 1 being N-4(4'-hydroxyphenylbutyryl)-L-prolyl-D,L-α-methyl-3,4-dimethoxyphenylalanine-3-quanidinopropylamide or a pharmaceutically acceptable salt thereof.

9. A chemical compound of the structural formula:

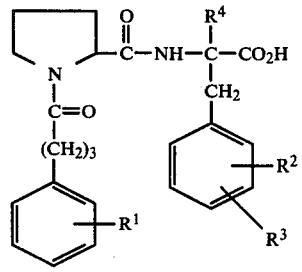

in which:
R$^1$, R$^2$ and R$^3$ are each hydrogen, hydroxy or methoxy; and
R$^4$ is lower alkyl of 1–3 carbons.

10. A pharmaceutical composition capable of improving kidney function comprising a nontoxic, pharmaceutically effective therefor quantity of a compound of claims 1, 2, 3, 4, 5, 6, 7 or 8 combined with a pharmaceutical carrier adapted for oral, anal or injectable administration.

11. A method of improving kidney function in a patient in need thereof comprising administering orally, anally or parenterally to a said patient a nontoxic quantity of a compound of claims 1, 2, 3, 4, 5, 6, 7 or 8 which is effective therefor.

* * * * *